United States Patent [19]

Murayama et al.

[11] Patent Number: 5,063,250

[45] Date of Patent: Nov. 5, 1991

[54] PROCESS FOR THE PRODUCTION OF METHANOL

[75] Inventors: Katsutoshi Murayama, Niigata; Hideaki Nagai, Tokyo, both of Japan

[73] Assignees: Mitsubishi Gas Chemical Company Inc.; Mitsubishi Jukogyo Kabushiki Kaisha, both of Tokyo, Japan

[21] Appl. No.: 573,285

[22] Filed: Aug. 27, 1990

Related U.S. Application Data

[63] Continuation of Ser. No. 293,898, Jan. 5, 1989.

[30] Foreign Application Priority Data

Jan. 12, 1988 [JP] Japan .................................. 63-3092

[51] Int. Cl.$^5$ ........................ C07C 27/96; C07C 31/04
[52] U.S. Cl. ................................................... 518/704
[58] Field of Search ........................................ 518/704

[56] References Cited

U.S. PATENT DOCUMENTS

| | | | |
|---|---|---|---|
| 3,763,205 | 10/1973 | Green | 518/704 |
| 4,238,403 | 12/1980 | Pinto | 518/704 |
| 4,455,394 | 6/1984 | Pinto | 518/704 |

FOREIGN PATENT DOCUMENTS 55-139492 10/1980 Japan .
60-245997 12/1985 Japan .

OTHER PUBLICATIONS

Quantulli, Hydrocarbon Processing, Oct. 1975, 94–99.
Kirk–Othmer, Incyclopedia of Chemical Technology, J. Wiley & Sons, New York 2nd edition, vol. 13, pp. 386–388.

*Primary Examiner*—Howard T. Mars
*Attorney, Agent, or Firm*—Wenderoth, Lind & Ponack

[57] ABSTRACT

This invention provides a process for the production of methanol which comprises steps of (a) reacting hydrocarbon with steam to generate synthesis gas composed of hydrogen, carbon monoxide and carbon dioxide as main components, (b) reacting the synthesis gas on a methanol synthesis catalyst to synthesize crude methanol, and (c) feeding the resultant crude methanol directly to a distillation column and distilling the crude methanol to separate prified methanol and an effluent water containing all or part of low boiling organic compounds, high boiling organic compounds and organic acids, the above step (c) being a step for the distillation and separation carried out without adding any alkali compound to neutralize the organic acids in the crude methanol obtained in the above step (b), the process including a step of bringing the effluent water resulting from the above step (c) into contact with gaseous hydrocarbon to humidify the hydrocarbon, the humidified hydrocarbon being used as a material for hydrocarbon and steam used in the above step (a).

4 Claims, 2 Drawing Sheets

PROCESS FOR THE PRODUCTION OF METHANOL

This application is a continuation of now abandoned application, Ser. No. 07/293,898 filed on Jan. 5, 1989.

FIELD OF THE INVENTION

This invention relates to a process for the production of methanol from hydrocarbon, and more specifically it relates to a process for the production of methanol, said process improved so as to reduce an amount of effluent water from an apparatus for the production of methanol and to save and reduce boiler water.

PRIOR ART OF THE INVENTION

A process for the production of methanol from hydrocarbon is carried out, in general, in the following steps.

(1) Synthesis gas-generation step which comprises reacting gaseous hydrocarbon or hydrocarbon vaporized from its liquid form with steam in the presence of a nickel-containing catalyst at 800° to 1,000° C. in a reforming furnace to prepare a synthesis gas composed of hydrogen, carbon monoxide and carbon dioxide as main components.

(2) Methanol synthesis step which comprises reacting the above methanol-synthesis gas on a copper-containing methanol synthesis catalyst under a pressure of 50 to 150 atm at a temperature of 200° to 300° C. to recover the resultant crude methanol in the liquid form from the reacted gas.

(3) Distillation step which comprises distilling the above crude methanol in the liquid form by distillation column or columns to separate purified methanol from effluent water (to be sometimes referred to as "effluent" hereinbelow) containing organic compounds having a lower boiling point than methanol (to be referred to as "low boiling organic compound" hereinbelow) and organic compounds having a higher boiling point than methanol (to be referred to as "high boiling organic compound" hereinbelow).

The synthesis gas-generating step, usually, uses steam in an amount equivalent to about three times the number of carbon atoms of a hydrocarbon as a material, and part of the hydrocarbons are decomposed to carbon dioxides. A major part of the carbon dioxides are converted to carbon monoxides and water by a shift reaction in the presence of a copper-containing catalyst in the methanol synthesis step. Water formed by the conversion is contained in crude methanol in the liquid form together with methanol, and separated at the next distillation step.

As mentioned above, a large amount of water is necessary for the production of methanol, heat generated in the steps for methanol production is used to produce steam from high purity water, and the steam is used in the methanol synthesis gas-generating step. On the other hand, water is separated in the distillation step and exhausted from the system.

There are many proposals to reduce steam necessary for the synthesis gas-generating step. For example, U.S. Pat. No. 4,238,403 describes a process for humidifying hydrocarbon by feeding hot water heated by combustion gas of a reforming furnace to a packed column. And Japanese Laid-Open Patent Publication No. 139492/1980 describes a process for evaporating water which comprises feeding hydrocarbon and water to a heat exchanger-type humidifier (which is also referred to as an evaporator) to evaporate water under heat by synthesis gas or exhaust gas. Japanese Laid-Open Patent Publication No. 245997/1985 describes a humidifier for humidifying hydrocarbon, which is formed by combining a packed column and a wetted wall column to be externally heated.

Further, U.S. Pat. No. 4,455,394 describes a process which comprises bringing a high-boiling organic compound (fusel oil) separated in the distillation step into contact with a gas phase flow of hydrocarbon to convert the above high boiling organic compound to a synthesis gas. In this U.S. Patent, it is an essential requirement to add alkali in order to neutralize organic acids contained in a crude methanol obtained from a synthesis apparatus when the crude methanol is distilled. In order to prevent the above alkali from being included in the hydrocarbon gas phase flow as a material, the fusel oil is incompletely evaporated. However, the inclusion of a very small amount of an alkali content in the hydrocarbon gas phase flow is inevitable. And an alkali liquid is extracted from the side portion of a humidifier (shown as 24 in drawings described in said Patent), and yet the fusel oil which stays unevaporated is included in the alkali liquid. Hence, this alkali liquid needs to be subjected to effluent treatment.

It is described in the above U.S. Patent that water at the bottom of a rectification column can be mixed with a fusel oil (by a pump 67 in the drawings described in said Patent) and supplied to the humidifier (column 7, lines 8 to 10 in said Patent). Since, however, the water at the bottom of the rectification column naturally contains the alkali, the alkali gets included in the hydrocarbon gas flow. If the alkali is contained in the hydrocarbon, many troubles are brought on a catalyst and a heat exchanger as will be discussed below. Therefore, in the flow shown in the above Patent, it is practically almost impossible to use water at the bottom of the rectification column in order to humidify hydrocarbon as a material.

As discussed above, an apparatus for the production of methanol requires a large amount of steam which is generated from expensive and high quality water. However, water separated in the distillation step contains the following impurity contents and cannot be utilized for generation of the above steam.

(1) Many high-boiling organic compounds such as higher alcohols having 3 or more carbon atoms and paraffins having 14 to 60 carbon atoms.
(2) Salts and esters of organic acids such as formic acid.
(3) Alkali metal salts.

The above salts and esters of organic acids are highly acidic and highly corrosive. For this reason, hydroxide or carbonate of alkali metal such as sodium hydroxide, sodium carbonate or the like is added for the neutralization in the distillation step as described, for example, in U.S. Pat. No. 4,455,394, and metal salts are contained in an effluent from the distillation step.

It is very difficult to remove the above impurities from the effluent from the distillation step, and it requires high costs to utilize water in the effluent as steam for production of the synthesis gas. Therefore, the effluent is thrown away without being reused.

Further, since the above effluent contains the above-mentioned impurity contents and is therefore socially detrimental, it is necessary to treat the effluent, e.g., by biological treatment, etc.

The effluent from the distillation step contains many organic compounds and need be treated, and such an effluent treatment needs high expenditure. And yet utilization of the effluent in the synthesis gas-generating step, if the utilization is possible, saves the amount of that steam for production of the synthesis gas which should be generated from expensive water. Hence, it has been desired to recover water from the effluent.

SUMMARY OF THE INVENTION

It is an object of this invention to provide an improved process for the production of methanol, in which the amount of the effluent from the methanol production device is reduced by using, in order to humidify hydrocarbon, the effluent resulting from the crude methanol-distillation step.

Further, it is another object of this invention to provide a process for the production of methanol, in which the amount of high purity boiler water used to generate steam to humidify hydrocarbon is reduced.

Further, it is another object of this invention to provide a process for the production of methanol, in which the unit consumption of hydrocarbon as a material is improved by using high boiling organic compounds and/or low boiling organic compounds contained in the above effluent as a source for methanol synthesis gas.

It is further another object of this invention to provide a process for the production of methanol, in which the treatment of the effluent is facilitated by reducing the amount of the effluent to be removed away from the system of methanol production steps.

According to this invention there is provided a process for the production of methanol which comprises steps of (a) reacting hydrocarbon with steam to generate synthesis gas composed of hydrogen, carbon monoxide and carbon dioxide as main components, (b) reacting the synthesis gas on a methanol synthesis catalyst to synthesize crude methanol, and (c) feeding the resultant crude methanol directly to a distillation column and distilling the crude methanol to separate purified methanol and an effluent water containing all or part of low boiling organic compounds, high boiling organic compounds and organic acids, the above step (c) being a step for the distillation and separation carried out without adding any alkali compound to neutralize the organic acids in the crude methanol obtained in the above step (b), the process including a step of bringing the effluent water resulting from the above step (c) into contact with gaseous hydrocarbon to humidify the hydrocarbon, the humidified hydrocarbon being used as a material for hydrocarbon and steam used in the above step (a).

DETAILED DESCRIPTION OF THE INVENTION

Figure 1:
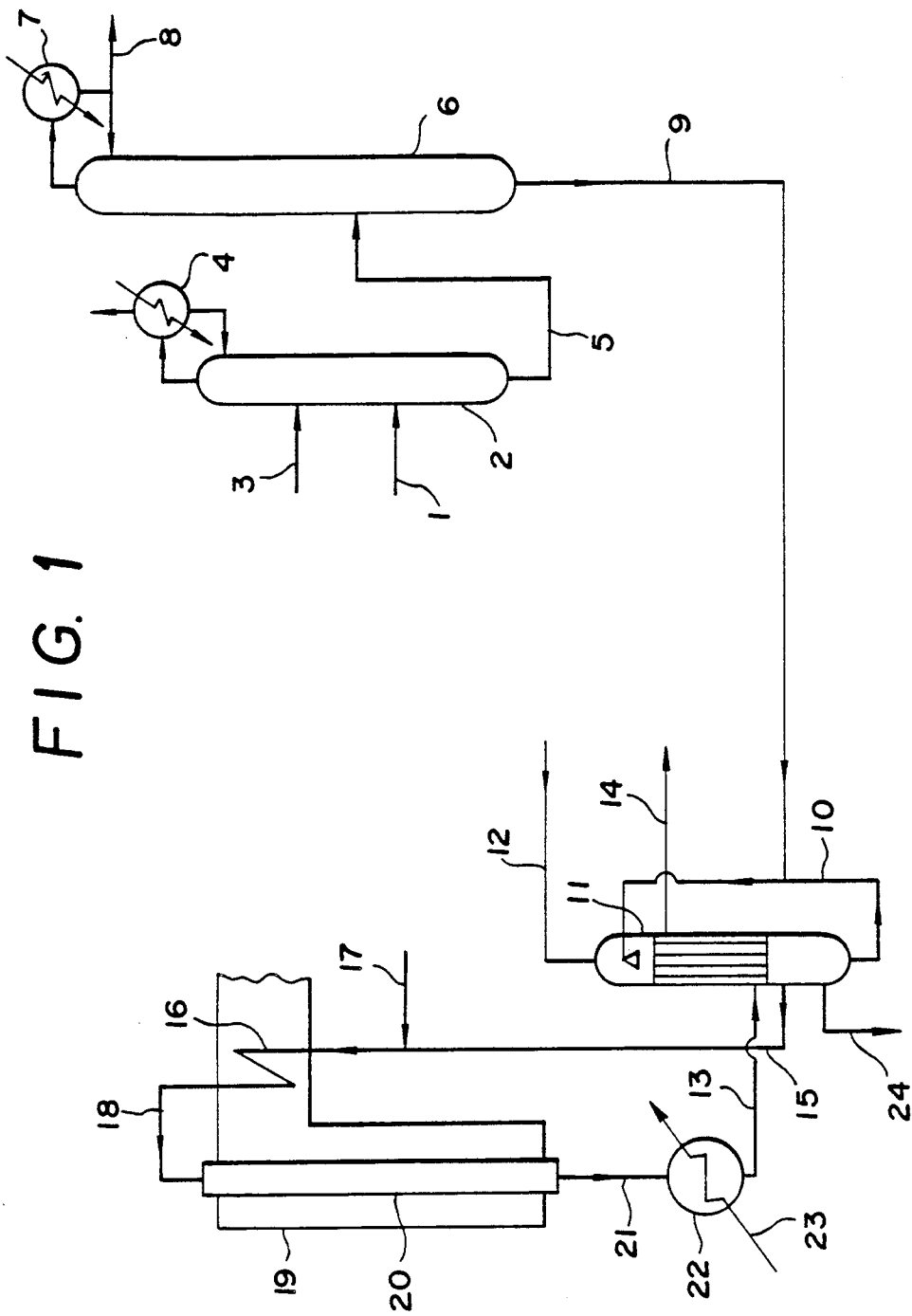
FIG. 1 shows one embodiment of the process for the production of methanol in this invention.

The present inventors have diligently made a study of how to use that effluent from the distillation step which has the above problems and, desirably, has to be recovered. As a result, it has been found that a major part of the effluent can be recovered and the boiler water and the steam for production of the synthesis gas can be saved by bringing the effluent into contact with gaseous hydrocarbon as a material to humidify the hydrocarbon without carrying out the conventinal neutralization with an alkali metal compound in the distillation step.

In this invention, the hydrocarbons as a material include gaseous natural gas and liquid LPG, naphtha, light-gravity oil, and the like.

The synthesis gas generation step by reacting hydrocarbon and steam includes a case of using a purge gas from the synthesis step as a part of the material together with hydrocarbon, a case of adding carbon dioxide to the material together with steam, and a case of adding oxygen-containing gas to carry out partial oxidation.

In the distillation step, the distillation is carried out, in general, by a two-column method which comprises feeding crude methanol obtained in the synthesis step to a first column to separate dissolved gases such as low boiling organic compounds, carbon dioxide, etc., out of its column top, and feeding methanol, water and high boiling organic compounds from the column bottom to a second distillation column to separate purified methanol out of its column top and organic acids-containing high boiling organic compounds and water out of its column bottom. And the distillation is also carried out by method using one column or three or more columns.

In this invention, the effluent which contains high boiling organic compounds and organic acids and which is brought into contact with gaseous hydrocarbon is an effluent which is separated out of the column bottom of the second column in the above two-column method, or which is separated out of the column bottom of the column in the above method using one column or three or more columns. Further, this invention also includes a case of extracting high boiling organic compounds and low boiling organic compounds from the middle stage of the distillation column to use these compounds and the effluent in order to humidify hydrocarbon.

The high boiling organic compounds and low boiling organic compounds extracted from the middle portion of the distillation column are usually subjected to incineration treatment. However, this invention can obviate the above incineration treatment. And since these organic compounds are used in the synthesis gas production step, the unit consumption of hydrocarbon as a material is improved.

The crude methanol obtained in the synthesis step includes methyl formate as a by-product, and methyl formate forms itself into formic acid by hydrolysis according to the following formula, and causes corrosion on an apparatus for the methanol synthesis.

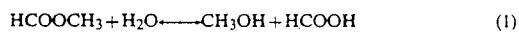

$$HCOOCH_3 + H_2O \longleftrightarrow CH_3OH + HCOOH \qquad (1)$$

In order to prevent the above corrosion, alkali addition is carried out in the vicinity of the feeding stage of the distillation column. As such alkali, hydroxides of alkali metals are usually used, and sodium hydroxide is used in particular in terms of effects and costs.

Formic acid is neutralized into sodium formate by addition of sodium hydroxide as shown in the following formula.

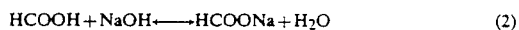

$$HCOOH + NaOH \longleftrightarrow HCOONa + H_2O \qquad (2)$$

For the above reason, the effluent from the distillation step contains sodium, and the contained sodium makes it difficult to use the effluent.

The humidifying of hydrocarbon makes it possible to effectively use low temperature heat sources at 150° to 300° C. in the synthesis gas generation step and the methanol synthesis step and saves the steam generated from the boiler water for the production of synthesis gas. Therefore, the study of employment of the above hydrocarbon humidifying is now under way in an apparatus for the production of methanol as mentioned above.

In the use of an effluent from the distillation step to humidify hydrocarbon, due to an alkali metal contained in the effluent, a mist of gas exhausted from a humidifier involves the alkali metal, contaminates a nickel-containing catalyst in a next reforming furnace for the production of the synthesis gas to lower the catalyst activity, and at the same time adheres to a preliminary heater and a reaction tube to cause degradation of heat conductivity performance and alkali corrosion. The amount of the adhered alkali metal is very small. However, it brings a serious damage on an apparatus for the methanol production since the apparatus is continuously operated for a long period of time.

Accordingly, it may be possible to consider a method using organic alkali in place of the hydroxides of alkali metals. Many organic alkalis (e.g., amines) are decomposed by a nickel-containing catalyst into gas which is not detrimental to the synthesis step. Since, however, their neutralization effects are small, they are used in large amounts, and they are expensive as compared with inorganic alkalis. Therefore, the use of organic alkalis is impractical.

In this invention, the neutralization treatment is not carried out in the distillation step. Hence, it is necessary to select an anti-corrosive material for the apparatus for the distillation step and for the humidifier, and a stainless steel material containing nickel and chrome is suitably used as such.

The material test conducted by the present inventors has showed that the use of materials containing components shown in the following Table 1 in portions of the distillation apparatus and humidifier can give corrosion resistance over 10 years.

TABLE 1

| Portions in use and maximum temperature | Main components and composition (%) | | | |
| --- | --- | --- | --- | --- |
| | Cr | Ni | Mo | C |
| Distillation apparatus | | | | |
| below 170° C. | 18–20 | 8–10.5 | | 0.08 or less |
| 170–200° C. | 18–20 | 8–10.5 | | 0.03 or less |
| Humidifier | | | | |
| below 200° C. | 18–20 | 8–10.5 | | 0.03 or less |
| 200–220° C. | 16–18 | 10–14 | 2–3 | 0.03 or less |
| 220–250° C. | 24–26 | 6–8 | 2–4 | 0.03 or less |

The humidifier usable in this invention is not specially limited. In the case of counter current contact method in which water is heated and charged onto the top of a packed column as shown, for example, in U.S. Pat. No. 4,238,403, a heat exchanger, water feeding pipe and pump also need be made of an expensive material. Therefore, it is costwise advantageous to use a heat exchanger-type humidifier which heats and evaporates water simultaneously as shown in Japanese Laid-Open Patent Publication No. 139492/1980.

And if hydrocarbon as a material is preliminarily heated to 250° to 430° C., humidified heat-insulatedly by an effluent from the distillation step and then humidified by high purity water containing no corrosive substance by using a heat exchanger-type humidifier, the result is that the effluent from the distillation step is evaporated at a low temperature. Thus, the above procedure is advantageous in terms of material quality, and it is not necessary, either, to use a higher quality material in the next heat-exchanger-type humidifier. In the heat-insulated humidifier, an effluent is sprayed by a sprayer in some cases. However, it is preferable to provide a packed bed in order to improve contact efficiency as shown, for example, in Japanese Laid-Open Patent Publication No. 245997/1985.

In addition, since many high boiling organic compounds, organic acids and inorganic substances have higher boiling points than water, these components are concentrated in the humidifier. Accordingly, there are risks that paraffins and inorganic substances adhere to a heat transfer tube to lower the efficiency, that the material is corroded due to an increase in concentration of the organic acids, and the like. Therefore, it is desirable to exhaust 1/10 to 1/20 of the amount of the charged effluent out of the system. Namely, in this invention, the amount of water exhausted from the distillation step is reduced to 1/10 to 1/20 of the amount resulting from the conventional process.

The following is an explanation of this invention according to drawings.

FIG. 1 shows one embodiment of this invention in which the effluent from the methanol distillation step is utilized in order to humidify hydrocarbon. In the FIG. 1, crude methanol from the synthesis step is supplied to the middle portion of a first distillation column 2 through a flow path 1, and sometimes a small amount of water from a flow path 3 is charged thereinto. Low boiling organic compounds are concentrated in the column top and partially concentrated in a condenser 4 to be refluxed, and its remaining portion is exhausted out of the system together with dissolved gases.

Methanol and water are existent in the bottom of the first distillation column 2 and supplied to a middle portion of a second distillation column 6 through a flow path 5. In the column top portion, methanol and water are cooled by a condenser 7 to cause a condensation, and methanol is purifed to a high degree of purity by maintaining a suitable reflux ratio. The resultant methanol as a product is taken out through a flow path 8 from the system. Water is mainly built up at the bottom of the second distillation column 6, and this water contains a small amount of high boiling organic compounds and organic acids and a very small amount of inorganic substances resulting from the apparatus. In the conventional process, hydroxide of alkali metal, etc., are supplied to the first distillation column 2, and therefore the bottom portion of the second distillation column contains alkali metal. Therefore, the effluent from the bottom of the second distillation column is exhausted out of the system of methanol preparation steps. In addition, the first distillation column 2 and the second distillation column 6 are provided with reboilers, respectively, to heat liquids in the columns. These reboilers are omitted since they have no direct relationship with the explanation here.

The effluent from the bottom of the second distillation column 6 is introduced through a flow path 9 into a recycle flow path 10, and then into the top of a heat exchanger-type humidifier 11. Preliminarily heated gaseous hydrocarbon as a material is introduced through a flow path 12, brought into contact with the effluent from the bottom of the second distillation column and humidified under heat by high temperature synthesis gas introduced through a flow path 13. The hot synthesis gas is used for heat recovery by the humidifier, then exhausted through a flow path 14 and supplied to the methanol synthesis step. The humidified hydrocarbon is exhausted through a flow path 15, and steam in an amount necessary for the process is added thereto through a flow path 17. Then, the hydrocarbon is preliminarily heated by a preliminary heater 16 located in a convection section of a reforming furnace 19 and directed into a reaction tube 20 packed with a nickel-containing catalyst. The synthesis gas from the reaction tube 20 was directed through a flow path 21, heat-exchanged in a heat exchanger 22 with boiler water from a flow path 23 to generate high pressure steam from said boiler water, and then enters a heat exchanger-type humidifier 11 through the flow path 13. In addition, part of the concentrated water is exhausted out of the system through a flow path 24.

Figure 2:
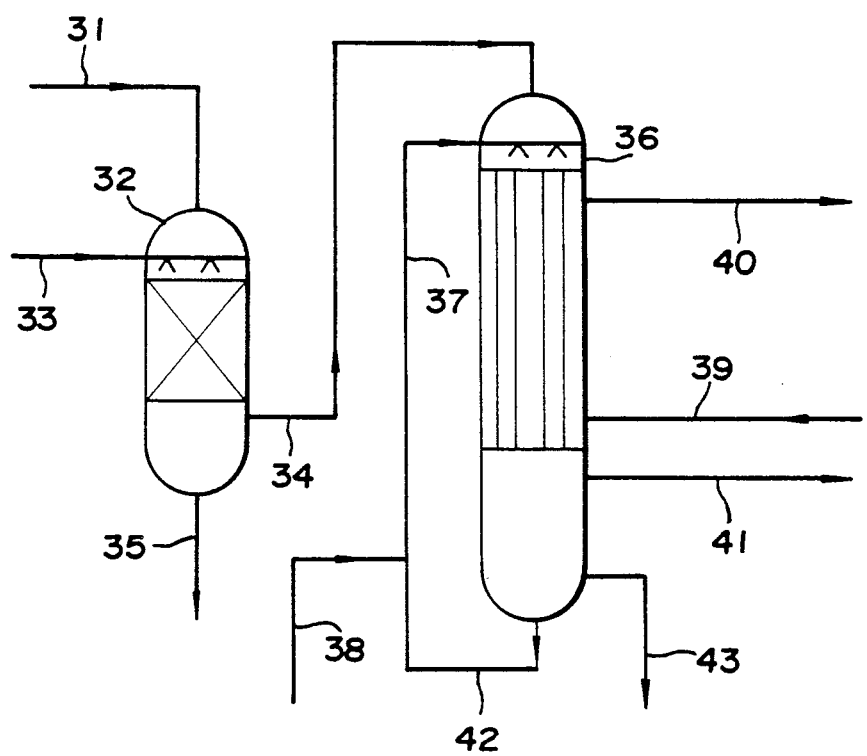
FIG. 2 shows one embodiment in which a heat-insulated humidifier is installed before the heat exchanger-type humidifier and the effluent from the distillation step is treated at a low temperature.

FIG. 2 shows a case where a heat-insulated humidifier is provided before a heat exchanger-type humidifier and an effluent from the distillation step is treated at a low temperature. Gaseous hydrocarbon heated to 250° to 430° C. is introduced through a flow path 31 to a heat-insulated humidifier 32, and brought into contact with effluent directed through a flow path 33 from the distillation step to be humidified. The heat-insulated humidifier 32 is provided with a packed bed to enhance contact efficiency. The effluent which is not evaporated in the heat-insulated humidifier is exhausted out of the system through a flow path 35. A part of the effluent which is not evaporated may be returned to the flow path 33.

Hydrocarbon humidified by the heat-insulated humidifier 32 enters a heat exchanger-type humidifier 36 through a flow path 34. This heat exchanger-type humidifier is supplied with high purity water through a flow path 38, and the above high purity water is supplied to the top portion of the humidifier through a flow path 37 together with water in circulation through a flow path 42 to humidify the hydrocarbon further, and introduced to a gas reforming furnace through a flow path 41. As a heat source for the heat exchanger-type humidifier, hot synthesis gas, which is heat-exchanged with boiler water, is used in the same way as shown in FIG. 1, and the hot synthesis gas is introduced through a flow path 39 for the heat recovery and then led through a flow path 40 to the methanol synthesis step. In addition, a part of water concentrated in the heat exchanger-type humidifier 36 is exhausted out of the system through a flow path 43. Water from the flow path 43 may be returned to the flow path 33.

The process for the production of methanol in this invention makes it possible to effectively use effluent from the distillation step, which was conventionally thrown away without being utilized, and said process has the following advantages.

(1) Since the effluent from the distillation step, which forms almost all portions of the effluent from the apparatus for the production of methanol, is reduced to 1/10 to 1/20, a burden of effluent treatment by biological treatment, etc., can be remarkably decreased.

(2) The amount of high purity boiler water is decreased. This advantage weighs more especially in methanol production in oil-producing countries located in dry parts of the world since water is precious.

(3) In the humidifier of this invention, not only the effluent from the distillation step but also the high boiling organic compounds and low boiling compounds are used for the humidifying. These high boiling organic compounds and low boiling organic compounds are usually subjected to incineration treatment. However, the process of this invention obviates the incineration treatment. Further, since these organic substances are supplied to the synthesis gas generation step, the unit consumption of hydrocarbon as a material is improved.

(4) When hydrocarbon preheated to 250° to 430° C. and the above effluent were contacted, humidified heat-insulatingly, and then humidified by high purity water by the use of a heat exchanger-type humidifier, the effluent is evaporated at a low temperature. Thus, advantage is given to the material quality of the heat-insulated humidifier, it is possible to increase the temperature for the humidifying of hydrocarbon without necessity to advance the material quality of the heat exchanger-type humidifier, and the amount of steam prepared from high purity boiler water can be effectively decreased.

Therefore, this invention has large industrial significance owing to the above advantages.

EXAMPLES

The following Examples will illustrate this invention.

EXAMPLE 1

In a flow shown in FIG. 1, 898 kg.mol/H of a crude methanol (645 kg.mol/H of methanol, 252 kg.mol/H of water and 1 kg.mol/H of other by-products) was supplied to a flow path 1 of a fisrt distillation column 2, and 59.2 kg.mol/H of water was poured into its flow path 3 to carry out the distillation. The column top was set at atmospheric pressure. And 1.2 kg of a mixture of low boiling compounds and methanol was extracted from the column top, and 956 kg.mol/H of a mixture mainly of methanol and water was extracted from the column bottom and supplied to a second distillation column 6.

In the second distillation column 6, again, its column top was set at atmospheric pressure, and 644.5 kg.mol/H of purified methanol (purity: 99.99 wt %) was extracted through a flow path 8 from the column top. And an effluent containing 311.2 kg.mol/H of water, 0.3 kg.mol/H of high boiling organic compounds and 125 wtppm of formic acid was extracted through a flow path 9 from the column bottom.

Effluent from the second distillation column was supplied through a flow path 10 to a heat exchanger-type humidifier 11, and a hydrocarbon gas having the following composition was introduced through a flow path 13 at a pressure of 16.3 kg/cm$^2$G and a temperature of 292° C.

| $CO_2$ | 0.40 mol % | $C_4H_{10}$ | 1.10 mol % |
| $CH_4$ | 88.10 | $C_5H_{12}$ | 0.35 |
| $C_2H_6$ | 6.39 | $C_6H_{14}$ | 0.27 |
| $C_3H_8$ | 2.48 | $N_2$ | 0.91 |

The temperature of effluent resting at the bottom of the heat exchanger-type humidifier 11 became 139° C., and 1,388 kg.mol/H of said effluent at the bottom was supplied to the humidifier top together with effluent from the second distillation column. As a heat source for this humidifier, 1,771.5 kg of a synthesis gas having the following composition was introduced through the flow path 13 at pressure of 12.7 kg/cm$^2$G and a temperature of 318° C., and exhausted through a flow path 14 at a temperature of 171° C.

| CO$_2$ | 5.76 mol % | CH$_4$ | 1.20 mol % |
|---|---|---|---|
| CO | 9.74 | N$_2$ | 0.13 |
| H$_2$ | 49.52 | H$_2$O | 33.56 |

In the above humidifier, water flowing down was heated to humidify hydrocarbon, 294.5 kg.mol/H of water was evaporated, and the temperature of the humidified hydrocarbon gas from the flow path 15 became 156° C.

In addition, in order to prevent impurities from being concentrated, 17.0 kg.mol/H of effluent was extracted through a flow path 24 to show that the effluent had a formic acid concentration of 500 wtppm.

In this Example, each of the distillation columns was made of SUS 304 in portions from its charging stage to column bottom and of SUS 316L in the liquid contact portion of its heat exchanger-type humidifier.

EXAMPLE 2

In the flow shown in FIG. 2, effluent containing 313 kg.mol/H of water, 0.3 kg.mol/H of high boiling organic compounds and 125 wtppm of formic acid was extracted from the bottom of a second distillation column at 110° C. in the same way as in Example 1, and the effluent was supplied to a heat-insulated humidifier 32 through a flow path 33.

A hydrocarbon gas having the following composition was supplied through a flow path 31 at a pressure of 16.5 kg/cm$^2$G and a temperature of 380° C.

| CO$_2$ | 0.40 mol % | C$_4$H$_{10}$ | 1.11 mol % |
|---|---|---|---|
| CH$_4$ | 88.20 | C$_5$H$_{12}$ | 0.36 |
| C$_2$H$_6$ | 6.29 | C$_6$H$_{14}$ | 0.28 |
| C$_3$H$_8$ | 2.39 | N$_2$ | 0.97 |

Consequently, the effluent in the distillation step was almost all evaporated, the hydrocarbon gas from a flow path 34 contained 284.6 kg.mol/H of steam, the pressure became 16.4 kg/cm$^2$G and the temperature became 144.1° C. The effluent exhausted from the system through a flow path 35 was 28.4 kg.mol/H of water, which contained 0.1 kg.mol/H of high boiling organic compounds and 1,000 wtppm of formic acid.

In a heat exchanger-type humidifier 36, 2,470 kg.mol/H of a synthesis gas having the following composition was supplied through a flow path 39 at a pressure of 12.7 kg/cm$^2$G and a temperature of 318° C. The flow path 40 had a temperature of 170° C.

| CO$_2$ | 5.76 mol % | CH$_4$ | 1.19 mol % |
|---|---|---|---|
| CO | 9.72 | N$_2$ | 0.14 |
| H$_2$ | 49.48 | H$_2$O | 33.71 |

The temperature at the bottom of the heat exchanger-type humidifier became 161.5° C. 828 kg.mol/H of water from a flow path 42 was extracted, and supplied onto the top of the humidifier through a flow path 37 together with 282 kg.mol/H of pure water heated to 120° C. from a flow path 38.

In a heat transfer tube, water flowing down was heated to humidify hydrocarbon, and 273.7 kg.mol/H of water was newly evaporated during the flowing course in the tube. The temperature of humidified hydrocarbon from a flow path 41 was 161° C. In order to prevent impurities from being concentrated in water to be used for the humidifying, 8.3 kg.mol/H of water was extracted through a flow path 43. The formic acid concentration in water from the flow path 38 was not more than 50 ppm.

In Example 2, each of the distillation columns was made of the same material as that in Example 1, and the heat exchanger-type humidifier and heat-insulated humidifier were made of SUS 304 since the operation temperatures were low.

What we claim is:

1. A process for the production of methanol from hydrocarbon, which comprises the steps of:
   (a) reacting hydrocarbon with steam to generate a synthesis gas composed of hydrogen, carbon monoxide and carbon dioxide as main components,
   (b) reacting the synthesis gas on a methanol synthesis catalyst to synthesize crude methanol,
   (c) feeding the crude methanol to a distillation column, without adding any alkaline compound to neutralize organic acids in the crude methanol, to distill the crude methanol and separate it into a purified methanol and effluent water containing low-boiling organic compounds, high-boiling organic compounds and organic acids, said distillation column composed of stainless steel having a composition of 18 to 20% by weight of Cr, 8 to 10.5% by weight of Ni and not more than 0.08% by weight of C in its portions contacting the low-boiling organic compounds, high-boiling organic compounds or organic acids,
   (d) bringing the effluent water into contact with preheated gaseous hydrocarbon in an apparatus composed of stainless steel having a composition of 16 to 26% by weight of Cr, 6 to 14% by weight of Ni, 2 to 4% by weight of Mo and not more than 0.03% by weight of C in its portions contacting the low-boiling organic compounds, high-boiling organic compounds or organic acids to humidify the hydrocarbon, and
   (e) feeding the humidified hydrocarbon for use in step (a),
   wherein step (d) contains
      a step of humidifying the hydrocarbon with the effluent water from step (c) by means of a heat exchanger humidifier using, as a heat source, heat of the synthesis gas generated in step (a), or
      a step of humidifying the hydrocarbon, pre-heated to 250° to 430° C., with the effluent water from step (c) by means of a heat-insulated humidifier, and then humidifying the hydrocarbon with water by means of a heat exchanger humidifier using, as a heat source, heat of the synthesis gas generated in step (a).

2. A process for the production of methanol according to claim 1, wherein steam is further added to the humidified hydrocarbon.

3. A process for the production of methanol according to claim 1, wherein the humidified hydrocarbon is humidified by the effluent water resulting from step (c) containing high boiling organic compounds and/or low boiling organic compounds extracted from the middle part of the distillation column in step (c).

4. A process for the production of methanol according to claim 1, wherein 1/10 to 1/20 of the effluent water resulting from step (c) is removed before the effluent water is used to humidify the hydrocarbon in step (d).

* * * * *